United States Patent
Park et al.

(10) Patent No.: US 11,452,794 B2
(45) Date of Patent: Sep. 27, 2022

(54) WOUND DRESSING MATERIAL COMPRISING FIBRILLATED ACCELLULAR DERMIS MATRIX AND BIODEGRADEABLE POLYMER, AND PREPARATION METHOD THEREFOR

(71) Applicants: CG BIO CO., LTD., Gyeonggi-do (KR); THE ASAN FOUNDATION, Seoul (KR)

(72) Inventors: Hee Jun Park, Seoul (KR); Hyun Seung Ryu, Gyeonggi-do (KR); Joon Pio Hong, Seoul (KR); Jun Hyuk Seo, Gyeonggi-do (KR); Jong Ha Park, Daejeon (KR); Soon Gee Hong, Jeollabuk-do (KR); Hak Su Jang, Gyeonggi-do (KR); So Myoung Lee, Gyeonggi-do (KR); Bo Young Yoo, Seoul (KR)

(73) Assignees: CG BIO CO., LTD., Gyeonggi-do (KR); THE ASAN FOUNDATION, Seoul (KR)

( * ) Notice: Subject to any disclaimer, the term of this patent is extended or adjusted under 35 U.S.C. 154(b) by 0 days.

(21) Appl. No.: 15/772,213

(22) PCT Filed: Oct. 28, 2016

(86) PCT No.: PCT/KR2016/012233
§ 371 (c)(1),
(2) Date: Apr. 30, 2018

(87) PCT Pub. No.: WO2017/074093
PCT Pub. Date: May 4, 2017

(65) Prior Publication Data
US 2018/0311399 A1    Nov. 1, 2018

(30) Foreign Application Priority Data

Oct. 28, 2015  (KR) .......................... 10-2015-0150465

(51) Int. Cl.
| | | |
|---|---|---|
| A61L 15/32 | (2006.01) |
| A61F 13/00 | (2006.01) |
| A61L 26/00 | (2006.01) |
| A61L 15/28 | (2006.01) |
| C07K 14/78 | (2006.01) |
| C08L 5/08 | (2006.01) |

(52) U.S. Cl.
CPC ............. *A61L 15/32* (2013.01); *A61F 13/00* (2013.01); *A61F 13/00012* (2013.01); *A61L 15/28* (2013.01); *A61L 26/0019* (2013.01); *A61L 26/0023* (2013.01); *A61L 26/0033* (2013.01); *A61L 26/0038* (2013.01); *A61L 26/0057* (2013.01); *C07K 14/78* (2013.01); *C08L 5/08* (2013.01); *A61L 2300/418* (2013.01); *C08L 2201/06* (2013.01); *C08L 2203/02* (2013.01)

(58) Field of Classification Search
CPC .... A61F 13/00; A61F 13/00012; A61L 15/28; A61L 15/40; A61L 15/32; C07K 14/78; C08L 5/08; C08L 2201/06; C08L 2203/02
See application file for complete search history.

(56) References Cited

U.S. PATENT DOCUMENTS

| | | | | |
|---|---|---|---|---|
| 2008/0181967 A1* | 7/2008 | Liu | ........................ | A61K 35/44 424/583 |
| 2010/0272782 A1* | 10/2010 | Owens | .................. | A61L 31/005 424/443 |
| 2011/0269667 A1* | 11/2011 | Shoseyov | .............. | A61K 38/39 514/1.8 |
| 2012/0263763 A1* | 10/2012 | Sun | ........................ | A61L 27/56 424/400 |
| 2012/0329034 A1 | 12/2012 | Wook et al. | | |
| 2013/0052257 A1* | 2/2013 | Al Mousa | ............... | A61L 15/46 424/445 |
| 2013/0280801 A1* | 10/2013 | Sun | ........................ | A61K 35/12 435/350 |

FOREIGN PATENT DOCUMENTS

| | | |
|---|---|---|
| KR | 100759488 B1 | 9/2007 |
| KR | 100791502 B1 | 1/2008 |
| KR | 10-2010-0009305 | 1/2010 |
| KR | 101089205 B1 | 12/2011 |
| KR | 101089614 B1 | 12/2011 |
| KR | 101523878 B1 | 5/2015 |
| WO | WO-03/017826 A2 | 3/2003 |

OTHER PUBLICATIONS

BeautyAnswered.com. "What are Cotton Balls." Retrieved Aug. 28, 2021. Retreived online <URL:https://www.beautyanswered.com/what-are-cotton-balls.htm>; 5 pages. (Year: 2021).*
International Search Report dated Feb. 2, 2017, issued in International Patent Application No. PCT/KR2016/012233, with English translation.
Ho, H., et al.; "Viscoelastic characterizations of acellular dermal matrix (ADM) preparations for use as injectable implants", Journal of Biomedical Materials Research, 2004, vol. 70A, No. 1, pp. 83-96.
Extended European Search Report dated May 21, 2019 in European Patent Application No. 16860276.1.

* cited by examiner

*Primary Examiner* — Doan T Phan
(74) *Attorney, Agent, or Firm* — Harness, Dickey & Pierce, P.L.C.

(57) ABSTRACT

The present invention relates to a wound dressing material comprising a fibrillated acellular dermis matrix and a biodegradable polymer aqueous solution and, more specifically, to: a wound dressing material comprising 5-20 wt % of a fibrillated acellular dermis matrix, 0.5-5 wt % of a biodegradable polymer, and 75-94.5 wt % of water; and a preparation method therefor.

10 Claims, 6 Drawing Sheets

WOUND DRESSING MATERIAL COMPRISING FIBRILLATED ACELLULAR DERMIS MATRIX AND BIODEGRADEABLE POLYMER, AND PREPARATION METHOD THEREFOR

CROSS-REFERENCE TO RELATED APPLICATIONS

This application is a national phase application of PCT Application No. PCT/KR2016/012233, filed on Oct. 28, 2016, which claims priority to Korean Patent Application No. 10-2015-0150465, Oct. 28, 2015. The entire disclosure of the applications identified in this paragraph is incorporated herein by reference.

FIELD

The present invention relates to a wound dressing comprising a fiberized acellular dermal matrix and a biocompatible polymer aqueous solution. More specifically, the present invention relates to a wound dressing comprising 5 to 20% by weight of fiberized acellular dermal matrix, 0.5 to 5% by weight of biocompatible polymer and 75 to 94.5% by weight of water, and a method for preparation thereof.

BACKGROUND

Wound is a state in which continuity of tissues is destroyed by external pressure. Wound healing process is generally divided into three (3) stages: inflammatory stage, proliferative stage and maturation stage. For wound healing, wound sites are covered from exposure to the external environment with an ideal dressing in order to prevent infection and suppress inflammatory response.

As biological dressing materials for treating wound, many dressing materials-which use the components of the human skin such as collagen and elastin in the dermis as a raw material—have been developed. In the case of collagen, it plays an important role as a major protein constituting tissues such as the bone and skin of the human body. 70% of the skin is composed of collagen, and collagen plays an important physiological role in tissue remodeling and wound healing. In addition, many studies have shown that collagen has an effect on wound healing. As an example of such biological dressing materials, Korean Patent Application Publication No. 10-2010-0009305 discloses a chitosan sponge in which the adherence capacity of cell adhesion proteins is increased by binding hydrophobic fatty acid group to chitosan and wound dressing using thereof.

Meanwhile, as one of the materials for treating wound caused by skin loss, acellular allogeneic dermis—which uses the skin tissue donated from a human cadaver—has been used. This is a safe material and has engraftment rate and healing effect which are far superior to synthetic materials. However, in the case of acellular allogeneic dermis processed from the skin donated from a human cadaver, there may be a difficulty in applying it according to the kind of wound, and there may be a difficulty in using it topically.

PRIOR DOCUMENT

Patent Document

Korean Patent Application Publication No. 10-2010-0009305

DETAILED DESCRIPTION

Technical Problem

Therefore, the technical problem of the present invention is the provision of a wound dressing in which acellular dermal matrix having high stability of tissue and minimized change of biological properties can be more easily applied to hardly applicable sites.

In addition, the technical problem of the present invention is the provision of a method for preparing said wound dressing.

Solution to Problem

To accomplish the object, the present invention provides a wound dressing comprising 5 to 20% by weight of fiberized acellular dermal matrix, 0.5 to 5% by weight of biocompatible polymer and 75 to 94.5% by weight of water.

In addition, the present invention provides a method for preparing a wound dressing which comprises:

pulverizing acellular dermal matrix to obtain fiberized acellular dermal matrix;

dissolving biocompatible polymer in water to obtain a biocompatible polymer aqueous solution;

mixing the fiberized acellular dermal matrix and the biocompatible polymer aqueous solution to obtain a mixture comprising 5 to 20% by weight of fiberized acellular dermal matrix, 0.5 to 5% by weight of biocompatible polymer and 75 to 94.5% by weight of water; and sterilizing the mixture.

DISCLOSURE OF THE INVENTION

Hereinafter, the present invention is described in more detail.

According to one aspect of the present invention, a wound dressing comprising 5 to 20% by weight of fiberized acellular dermal matrix, 0.5 to 5% by weight of biocompatible polymer and 75 to 94.5% by weight of water is provided.

The wound dressing according to the present invention comprises 5 to 20% by weight, preferably 7 to 15% by weight, and more preferably 8 to 12% by weight of fiberized acellular dermal matrix.

Acellular dermal matrix (ADM)—in which epidermis and cells in dermis of the skin tissue donated from a human cadaver are removed to avoid immunorejection—is widely used in reconstruction of soft tissues in this technical field and is also widely used in allograft for treating burns.

In the present invention, the fiberization of acellular dermal matrix is preferably carried out by the use of a cutting mill. In the present invention, the fiber length of fiberized acellular dermal matrix is preferably 200 to 1,000 μm.

In the present invention, if the fiberized acellular dermal matrix is comprised in an amount of less than 5% by weight, the effect for wound healing provided by acellular dermal matrix may be weak, and if the fiberized acellular dermal matrix is comprised in an amount of greater than 20% by weight, it may be economically undesirable since increasing the wound healing effect commensurately with the adding amount would not be expected.

The wound dressing according to the present invention comprises 0.5 to 5% by weight, preferably 0.8 to 3% by weight, and more preferably 1 to 2% by weight of biocompatible polymer.

In the present invention, the biocompatible polymer plays a role as a carrier to increase the viscosity of the wound dressing, and provides a moist environment at the time of application to wound sites.

In the present invention, the biocompatible polymer is preferably gelatin, hyaluronic acid, collagen, poloxamer or a mixture thereof, and is most preferably gelatin. In the present invention, when gelatin is used as the biocompatible polymer, a hemostatic effect provided therefrom may be expected. In the present invention, it is preferable that gelatin having the strength of 250 Bloom or more is used.

In the present invention, if the biocompatible polymer is comprised in an amount of less than 0.5% by weight, there may be a problem in that the wound dressing flows to sites other than the wound site due to the increase of flowability, and if the biocompatible polymer is comprised in an amount of greater than 5% by weight, there may be a problem in application of the wound dressing due to high viscosity.

The wound dressing according to the present invention comprises the balance of water—for example, 75 to 94.5% by weight, preferably 82 to 92.2% by weight, and more preferably 86 to 91% by weight of water.

The wound dressing according to the present invention is formulated into a dosage form of paste by mixing the fiberized acellular dermal matrix and the biocompatible polymer aqueous solution. The wound dressing according to the present invention preferably has the viscosity of 10,000 to 20,000 cP. In the present invention, if the viscosity of wound dressing is less than 10,000 cP, there may be a problem in formulating a dosage form of paste, and if the viscosity of wound dressing is greater than 20,000 cP, there may be a problem in applying the wound dressing.

According to another aspect of the present invention, a method for preparing a wound dressing which comprises the following steps is provided:

pulverizing acellular dermal matrix to obtain fiberized acellular dermal matrix;

dissolving biocompatible polymer in water to obtain a biocompatible polymer aqueous solution;

mixing the fiberized acellular dermal matrix and the biocompatible polymer aqueous solution to obtain a mixture comprising 5 to 20% by weight of fiberized acellular dermal matrix, 0.5 to 5% by weight of biocompatible polymer and 75 to 94.5% by weight of water; and sterilizing the mixture.

Methods for preparing acellular dermal matrix (ADM) are known in this technical field. For example, Korean Patent No. 10-1089614 (grant date: Nov. 29, 2011) discloses a method for preparing an acellular dermal matix comprising the steps of:

a) removing epidermis of allograft skin;

b) removing cells in dermis;

c) mixing glycerol, propylene glycol and a basic solvent or solution;

d) dissolving sucrose in the solution to a final concentration of 20 to 40% by weight to obtain a cryoprotectant;

e) penetrating the cryoprotectant into the skin from which epidermis and cells in dermis are removed; and f) freeze-drying the cryoprotectant-penetrated skin.

In said method, the mixing ratio of glycerol, propylene glycol and the basic solvent or solution is preferably 0.5~2: 0.5~2:6~10, based on weight.

In said method, the example of the basic solvent or solution includes, but is not limited to, distilled water, normal saline, PBS (phosphate-buffered saline), HBSS (Hank's balanced salt solution), TBS (Tris-buffered saline), TAPS (N-Tris(hydroxymethyl)methyl-3-aminopropanesulfonic acid) buffer, Bicine (N,N-Bis(2-hydroxyethyl)glycine) buffer, HEPES (4-(2-hydroxyethyl)-1-piperazineethanesulfonic acid) buffer, TES (N-Tris(hydroxymethyl)methyl-2-aminoethanesulfonic acid) buffer, PIPES (piperazine-N,N'-bis(2-ethanesulfonic acid) buffer, cacodylate buffer, MES (2-(N-morpholino)ethanesulfonic acid) buffer. MEM (Minimum Essential Media), DMEM (Dulbecco's Modified Eagle Media), RPMI 1640. IMDM (Iscove's Modified Dulbecco's Media), Defined Keratinocyte-SFM (without BPE (bovine pituitary extract)), Keratinocyte-SFM (with BPE), KnockOut D-MEM, AminoMAX-II Complete Medium, AminoMAX-C100 Complete Medium and a mixture thereof.

In said method, the final concentration of sucrose is most preferably 30% by weight.

In said method, the penetration of the cryoprotectant into the separated skin is preferably carried out in a 4° C. low-temperature bath for 6 to 24 hours.

In said method, the freezing of the cryoprotectant-penetrated skin is carried out preferably −0.1° C. to −5° C. per minute, and most preferably −1° C. per minute.

Figure 1:
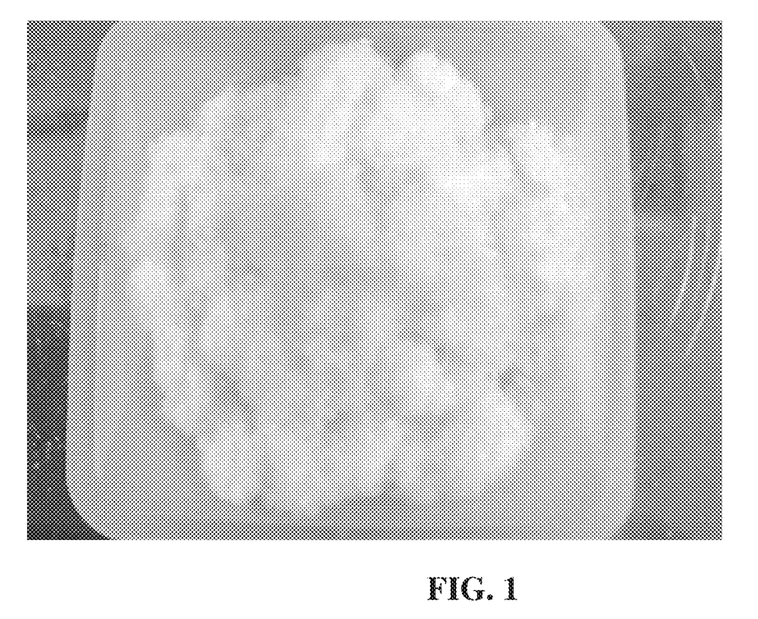
FIG. 1 is a photograph of the fiberized acellular dermal matrix in the form of cotton.
Figure 2:
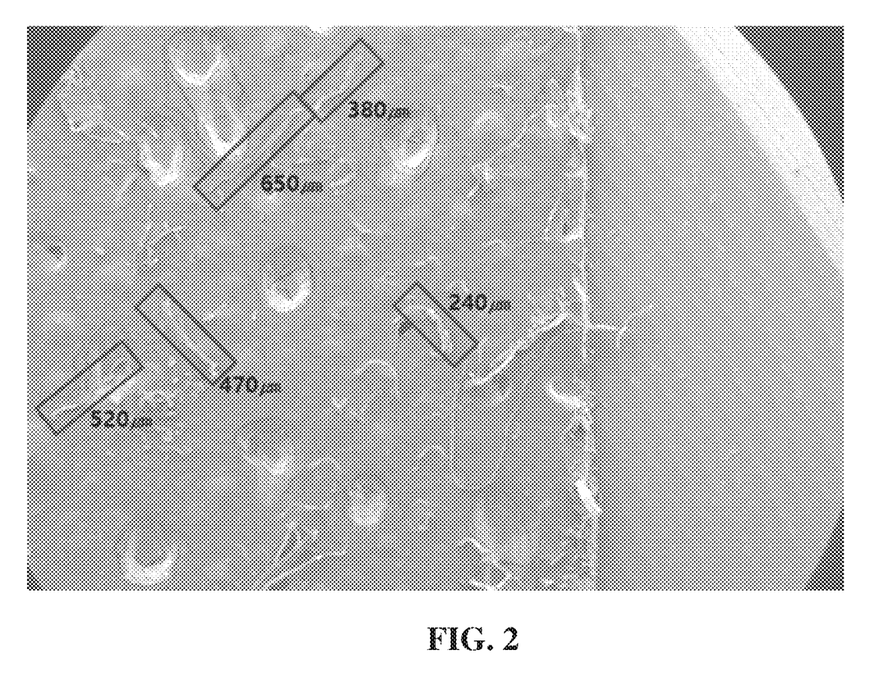
FIG. 2 is a scanning electron microscope photograph of the fiberized acellular dermal matrix in the form of cotton.
Figure 3:
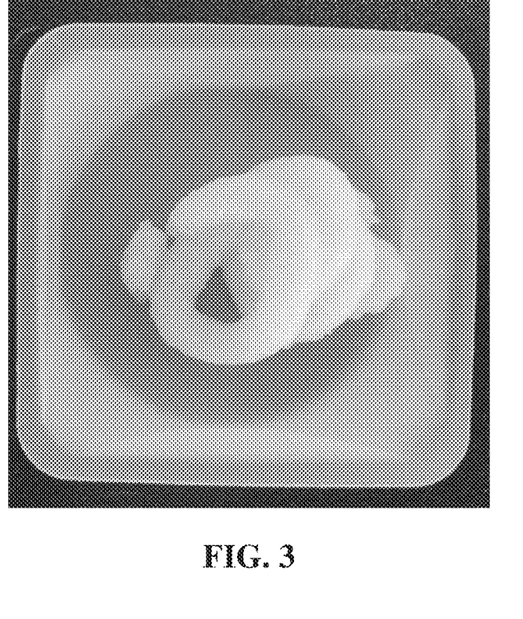
FIG. 3 is a photograph of the wound dressing prepared by mixing the fiberized acellular dermal matrix and gelatin aqueous solution in the form of paste.

In the present invention, the fiberization of acellular dermal matrix is preferably carried out by the use of a cutting mill. In the present invention, the acellular dermal matrix pulverized in the form of cotton can be obtained by the fiberization in which a cutting mill is used (FIG. 1). To fiberize acellular dermal matrix in the form of cotton by the use of a cutting mill, it is preferable that the thickness of acellular dermal matrix is 1 mm or more, and that there is proper moisture in the tissues. Moisture in the tissues is, for example, about 10%. The fiberized acellular dermal matrix in the form of cotton is appropriate to formulate a paste dosage form at the time of mixing with the biocompatible polymer aqueous solution. In the present invention, the fiber length of fiberized acellular dermal matrix is preferably 200 to 1,000 µm.

In the method for preparing a wound dressing according to the present invention, dissolving biocompatible polymer in water is preferably carried out at a high temperature of 50 to 70° C.

In the method for preparing a wound dressing according to the present invention, the sterilization of the mixture of the fiberized acellular dermal matrix and the biocompatible polymer aqueous solution may be carried out by methods conventionally used in this technical field, and preferably by radiation sterilization. For example, the sterilization may be carried out by electron beam (e-beam).

Effects of the Invention

The wound dressing according to the present invention can be easily applied to sites where conventional acellular dermal matrix has difficulty in application or topical sites, protect wound sites from external contaminants via high moisture content and viscosity, and maintain moist environment, thereby efficiently helping the treatment of wound sites.

BEST MODES FOR CARRYING OUT THE INVENTION

Hereinafter, the present invention is explained in more detail with the following examples. However, the following examples are only intended to facilitate understanding of the present invention, and the protection scope of the present invention is not limited thereto.

Because human skin tissue harvested from a donor (cadaver) is prohibited from being used in an experiment, pig skin—which is the closest to human skin—is used for preparing samples according to the method of the following Example.

Example (1) Pig skin was washed with saline solution.
(2) The pig skin was cut at the size of 5×10 cm$^2$.
(3) The pig skin was immersed in 1M NaCl (Sigma, USA) solution.
(4) A 38° C. incubator (P-039, CoreTech, Korea) was prepared.
(5) The reaction of the pig skin immersed in 1M NaCl (Sigma, USA) solution was carried out in the 38° C. incubator (P-039, CoreTech, Korea) with stirring for about 6 to 24 hours.
(6) Epidermis was removed by using forceps.
(7) The dermis from which the epidermis has been removed was washed with phosphate-buffered saline.
(8) The washed dermis was immersed in 0.5% SDS and reacted with stirring at room temperature for 1 hour to remove cells from the dermis.
(9) The dermis from which cells have been removed was washed with phosphate-buffered saline.
(10) Glycerol (Sigma. USA), propylene glycol (Sigma, USA) and phosphate-buffered saline (Gibco, USA) were mixed in the weight ratio of 1:1:8.
(11) Sucrose (Sigma. USA) was added to the solution of step (10) as the final concentration of 30% by weight and dissolved to obtain a cryoprotectant.
(12) A low-temperature bath (P-039. CoreTech, Korea) was set at 4° C.
(13) The pig skin of step (9) was put in the 4° C. low-temperature bath, and then the cryoprotectant was penetrated into the pig skin for 12 hours.
(14) The penetration-completed pig skin was put in a Tyvek bag (Korea C&S Co., Ltd., Korea).
(15) A freezing dryer (Genesis 25XL, VirTis, USA) was prepared.
(16) The Tyvek bag of step (14) was put in the freezing dryer and frozen to −70° C. at the rate of −1° C. per minute, and then dried under the vacuum of 5 torr for 24 hours to obtain a freeze-dried acellular dermal matrix.
(17) The freeze-dried acellular dermal matrix was pulverized and fiberized by the use of a cutting mill (Pulverisette19, FRITSCH, Germany).
(18) To 1.25 g of gelatin water was added to make 100 ml, and gelatin was dissolved at 60° C. to obtain a gelatin aqueous solution.
(19) 11 g of the fiberized acellular dermal matrix of step (17) was mixed with 89 g of the gelatin aqueous solution of step (18) to prepare a paste.
(20) The paste of step (19) was put into a syringe and double-packaged with a P.E.T tray and Tyvek bag, and sterilization was then carried out by e-beam irradiation.

Experimental Example 1: Measurement of Viscosity

Measurement of viscosity was carried out by measuring the torque required to rotate a disk in a fluid according to a rotational viscometer test. The following method was repeated six (6) times, and the results are represented in Table 1.

(1) To measure the viscosity at room temperature (25° C.), a rotational viscometer was set at 25° C. by the use of a circulator.
(2) 1 ml of samples was put into the rotational viscometer, and a disk was rotated to measure the viscosity value due to the torque.

TABLE 1

| No. | Viscosity (cP) |
| --- | --- |
| 1 | 15069.00 |
| 2 | 13024.58 |
| 3 | 16210.50 |
| 4 | 14671.25 |
| 5 | 13444.00 |
| 6 | 16396.00 |
| Aver. | 15158.15 |

Experimental Example 2: Measurement of Loss on Drying

Loss on drying was measured by the following method, and the results are represented in Table 2.

(1) Samples (about 1 g) were put into the weighing bottles, and the weights of initial weighing bottles and samples were measured.
(2) After drying at 105° C. for 4 hours, the weights of the weighing bottles containing the samples were measured.
(3) Loss on drying was determined with the weights of before and after drying by the use of the following equation.

$$\frac{a+b-c}{b} \times 100$$

a: initial weight of weighing bottle
b: weight of sample
c: weight of weighing bottle and sample after drying at 105° C. for 4 hours.

TABLE 2

| Criteria | | C0002A1 | | | C0003A1 | | | C0004A1 | | |
|---|---|---|---|---|---|---|---|---|---|---|
| Measured | a | 143.3997 | 144.9985 | 143.4826 | 143.5162 | 143.4552 | 144.3332 | 143.2802 | 143.9697 | 143.1487 |
| value (g) | b | 1.0262 | 1.0084 | 1.0442 | 1.0327 | 1.0234 | 1.0259 | 0.9973 | 1.0273 | 1.0482 |
| | c | 143.51 | 145.1852 | 143.6485 | 143.6344 | 143.5955 | 144.4665 | 143.4587 | 144.1157 | 143.3372 |
| Result (%) | | 89.25 | 81.49 | 84.11 | 88.55 | 86.29 | 87.01 | 82.10 | 85.79 | 82.02 |

Experimental Example 3: Evaluation of Efficacy on Impaired Skin Regeneration

According to the following Table 3, 6-week-old Sprague-Dawley rats were divided into each group. A collagen sponge was prepared by freeze-drying bovine collagen (Bioland, Korea) and using carbodiamide as a crosslinking agent, and Madecassol, a commercially available product (Dongkook Pharmaceutical Co., Ltd., Korea), was purchased. Experimentation was carried out at the SPF Laboratory Animal Center of Dongguk University Biomedi Campus.

TABLE 3

| Group | Criteria |
|---|---|
| Example | Paste prepared in Example 1 ml |
| Control 1 | Madecassol 1 ml |
| Control 2 | Gelatin 1 ml |
| Control 3 | Collagen sponge (diameter: 20 mm) |
| Positive Control | Normal rat |
| Negative Control | Removal of whole layers of skin |

At 2 wounds of each rat, the Example and Controls were applied or grafted. To prevent loss of the graft, at the wound sites the primary dressing was carried out with Tegaderm™ (3M), and the secondary dressing was carried out with a compression bandage. For about 10 days when exudate was produced, dressings were changed every day.

Figure 4:
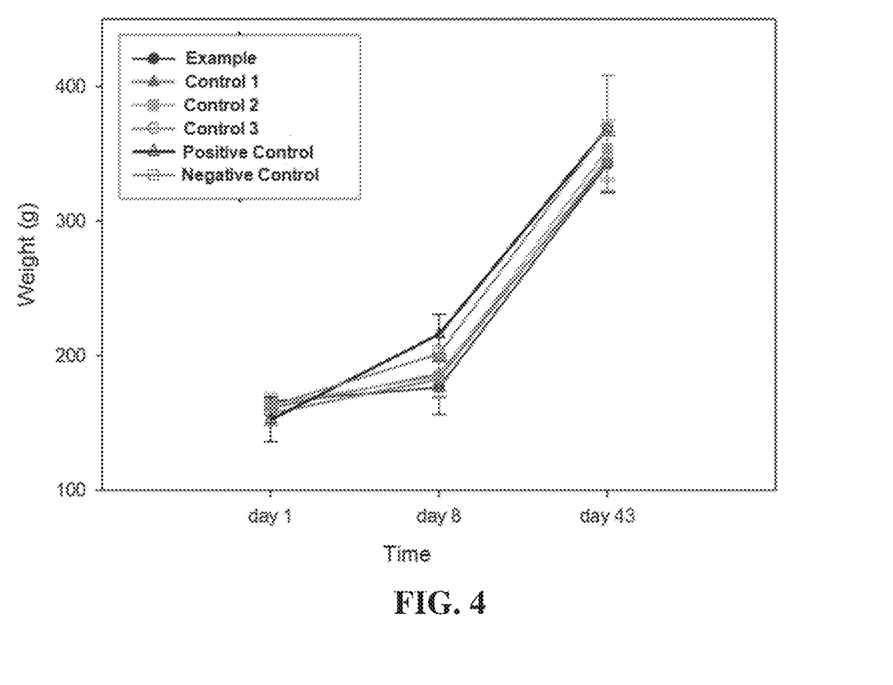
FIG. 4 is a graph representing the change of body weight according to elapsed time in rats of each group of Experimental Example 3.

The body weight of each rat was measured, and the results are represented in FIG. 4. The difference of the body weight between normal rats of the Positive Control and experimental groups was within 20%, and so there was no change in the body weight due to operation and dressing.

3-1. Evaluation of Wound Contraction Percentage and Dermal Regeneration

Figure 5:
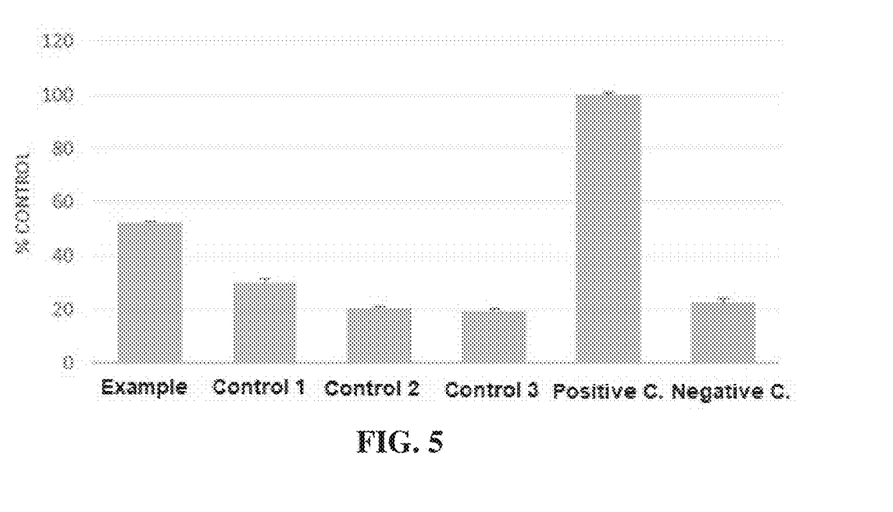
FIG. 5 is a graph representing wound contraction percentage.

Wound areas were calculated by a Leopard program, and the results are represented in FIG. 5 as wound contraction percentages. In addition, those results as well as the results of dermal regeneration are represented in the following Table 4.

TABLE 4

| | Negative Control | Example | Control 1 | Control 2 | Control 3 |
|---|---|---|---|---|---|
| Wound contraction | 85% | 50% | 70-80% | 80-85% | 70% |
| Dermal regeneration | ++ | ++++ | ++ | ++ | +++ |

As can be seen from the above results, the paste of the Example shows much better effect as compared with the control groups.

3-2. Histological Observation (H&E Staining and MT Staining)

After 6-week experimentation, the animals were sacrificed, and the tissues including wound sites were removed. After 24-hour fixation in 10% neutral buffered formalin solution, the tissues impaired by burns were taken, dehydrated and embedded in paraffin. The tissues were sectioned at the thickness of 5 μm with a microtome and attached to slides. After deparaffinization and rehydration processes, hematoxylin-eosin (H&E) staining and Masson's trichrome (MT) staining were carried out.

In the case of H&E staining, paraffin was removed from the tissue sections with xylene, and the tissue sections were rehydrated with 100, 90, 80, 70% ethanol and distilled water for 5 minutes each. After rinsing with distilled water, the tissues were used. After staining with Harris hematoxylin for 3 minutes, the tissues were rinsed with distilled water for 5 minutes. After washing, the tissues were stained with eosin for 5 minutes, dehydrated with 70, 80, 90, 100% ethanol and xylene, and mounted with Shandon Synthetic Mountant (Thermo Scientific, USA). In the case of MT staining, paraffin was removed from the tissue sections with xylene, and the tissue sections were rehydrated with 100, 90, 80, 70% ethanol and distilled water for 5 minutes each. After rinsing with distilled water, the tissues were used. After reaction with 60° C. Bouin's solution (IMEB, USA) for 1 hour, the tissues were rinsed with distilled water. After reaction and washing, the tissues were again treated with Biebrich scarlet-acid fuchsin, phosphomolybdic-phosphotungstic acid and aniline blue stain solution (IMEB, USA) for 5 minutes each, and rinsed with distilled water. The tissues were dehydrated with 70, 80, 90, 100% ethanol and xylene, and mounted with Shandon Synthetic Mountant (Thermo Scientific, USA).

Figure 6:
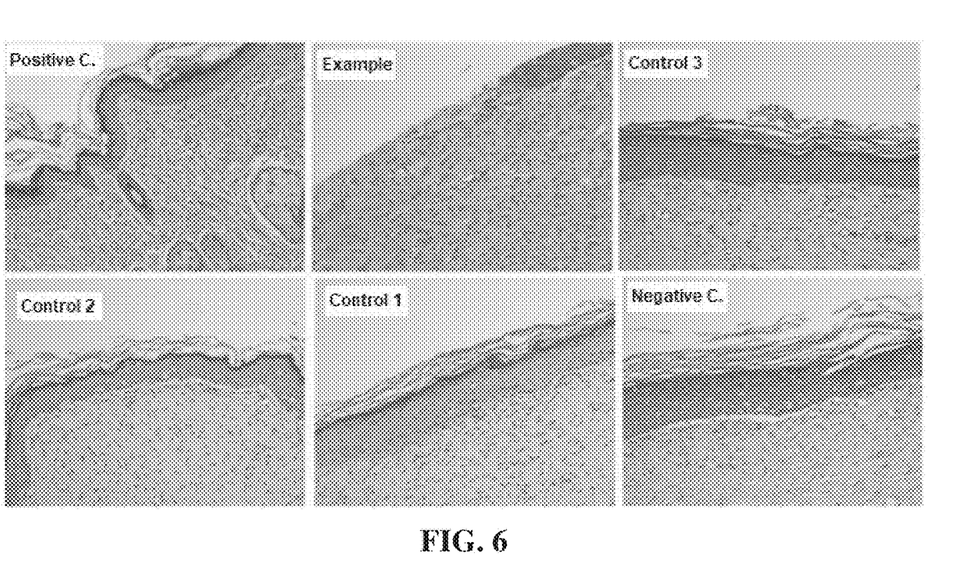
FIG. 6 is optical microscope photographs of the tissues obtained after 6 weeks of wound healing with H&E staining and 100× magnification.
Figure 7:
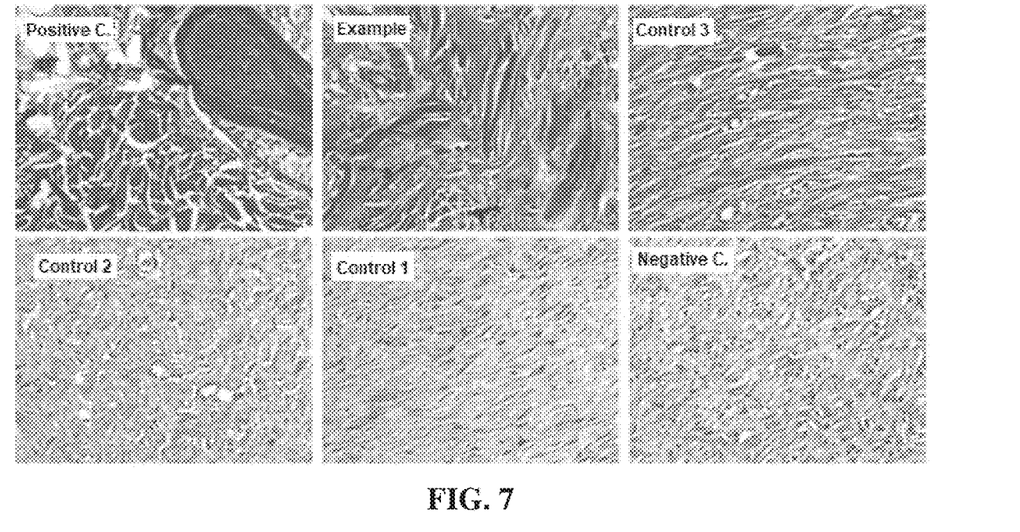
FIG. 7 is optical microscope photographs of the tissues obtained after 6 weeks of wound healing with MT staining and 200× magnification.

The results of H&E staining and MT staining are represented in FIGS. 6 and 7, respectively. From FIG. 6, it can be known that in the Example group although regeneration did not reach to the epidermal layer, new blood vessels, fibroblasts, monocytes and some macrophages were observed in the dermal layer. From FIG. 7, it can be known that because of initial regeneration of the dermis in the Example group, the regeneration of collagen fiber was thicker than in the other groups.

3-3. CD 31 Immunostaining

In the process of healing skin damage, angiogenesis is important. As such, to evaluate angiogenesis, the results of CD 31 immunostaining of the tissues 2 weeks and 6 weeks after experimentation are represented in FIGS. 8 and 9, respectively.

Figure 8:
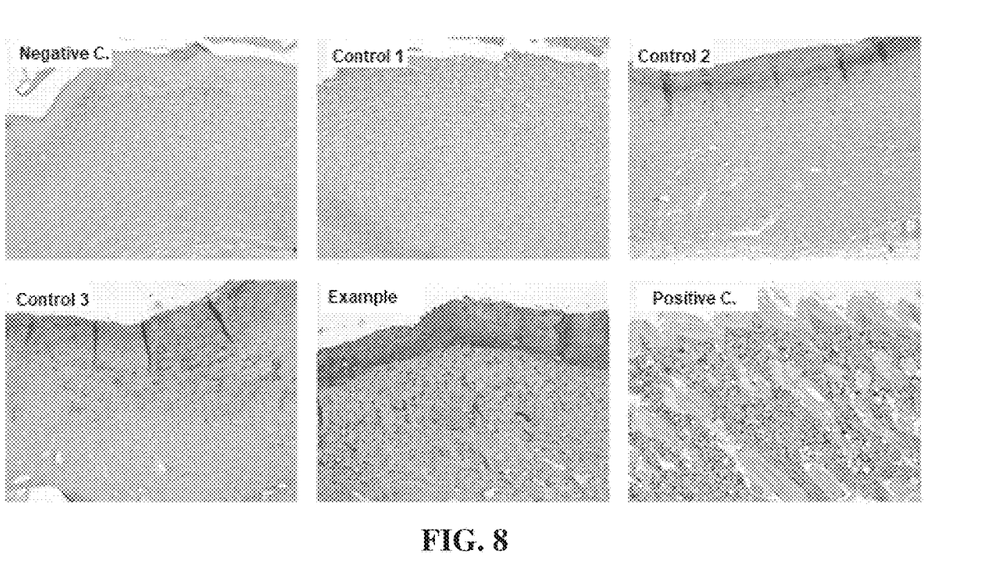
FIG. 8 is optical microscope photographs of the tissues obtained after 2 weeks of wound healing with CD31 immunostaining and 100× magnification.
Figure 9:
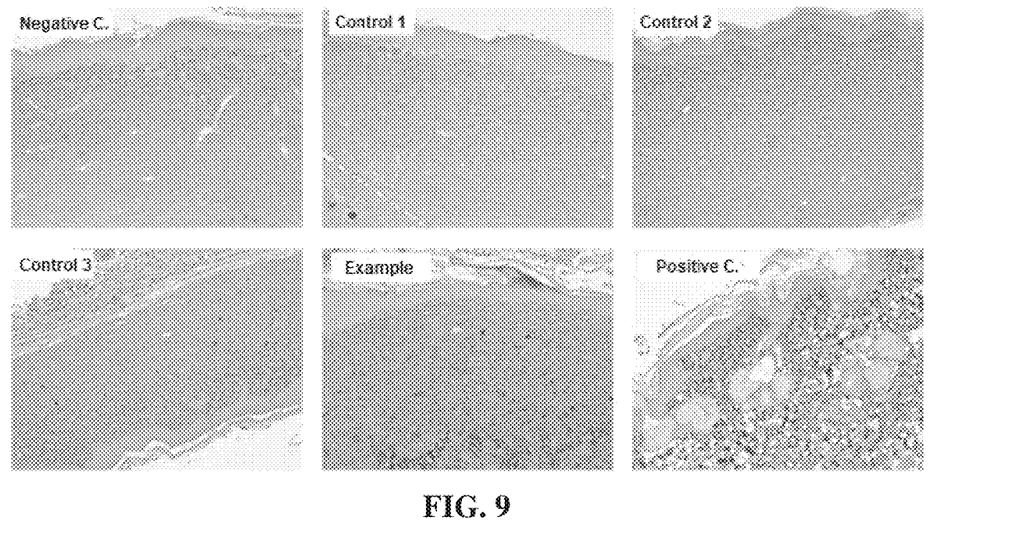
FIG. 9 is optical microscope photographs of the tissues obtained after 6 weeks of wound healing with CD31 immunostaining and 100× magnification.

As can be seen from FIG. 8, in the tissues 2 weeks after experimentation angiogenesis was not observed in the Negative Control and Control 1 groups, but new blood vessels in brown were observed in the Control 2 and Control 3 groups, and many invasion of new blood vessels was observed in the Example group. As can be seen from FIG. 9, in the tissues 6 weeks after experimentation new blood vessels were not observed in other groups, but new blood vessels were still observed in the Example group. From this, it can be known that dermal regeneration was still progressing.

3-4. Victoria Blue Staining

Formation of elastin—which has an important effect on elasticity of the skin—plays an important role in completeness of dermal regeneration. Accordingly, to observe elastin formation in dermis 6 weeks after wound healing, Victoria blue staining was carried out, and the results are represented in FIG. 10.

Figure 10:
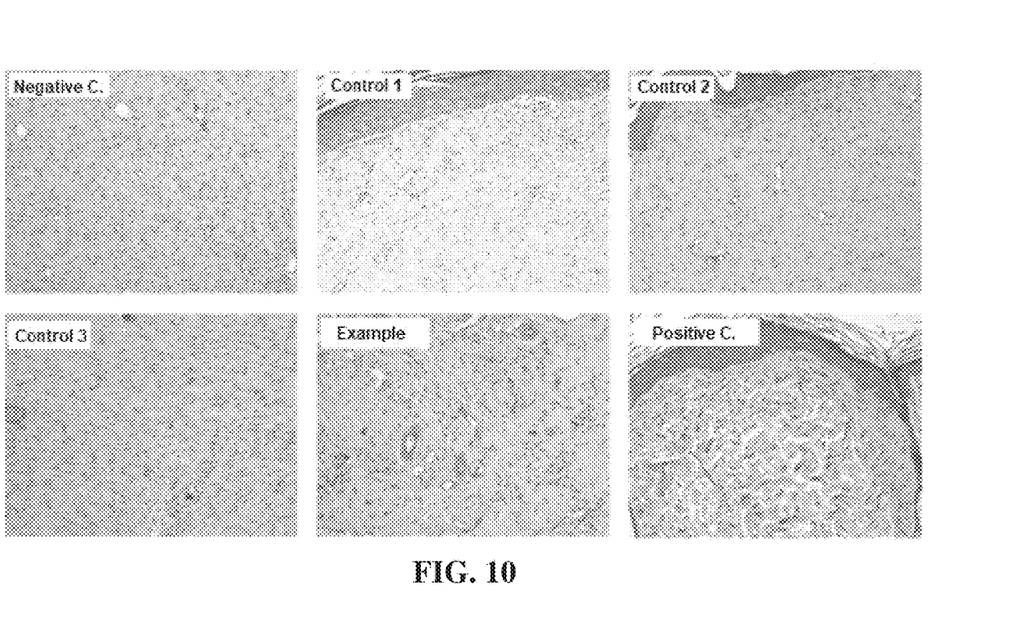
FIG. 10 is optical microscope photographs of the tissues obtained after 6 weeks of wound healing with Victoria blue staining and 100× magnification.

As can be seen from FIG. 10, in the Positive Control group and Example group elastin in blue was observed, and weak expression of elastin was observed in the Control 3 group.

3-5. Fibronectin Immunostaining

Fibronectin—which is extracellular matrix (ECM) having an important effect on elasticity of the skin—plays an important role in dermal regeneration. Accordingly, to observe fibronectin formation in dermis 6 weeks after wound healing, immunostaining was carried out, and the results are represented in FIG. 11.

Figure 11:
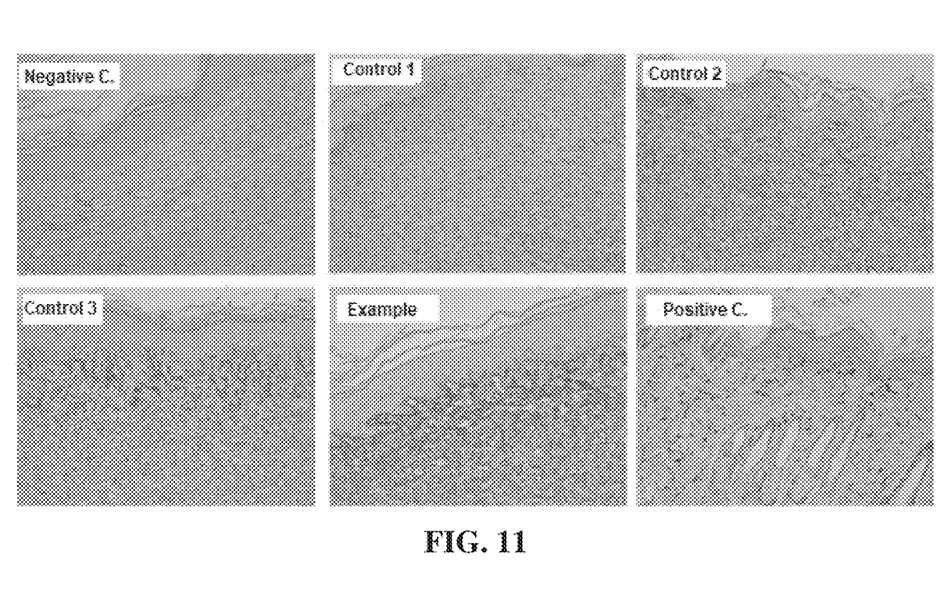
FIG. 11 is optical microscope photographs of the tissues obtained after 6 weeks of wound healing with fibronectin immunostaining and 100× magnification.

As can be seen from FIG. 11, in the Positive Control group and Example group fibronectin in brown was observed. However, in the Negative Control group and Control 1 group fibronectin was expressed very weakly.

3-6. Laminin Staining

The basement membrane between dermis and epidermis is important extracellular matrix (ECM) in epidermal regeneration. If the regeneration of basement membrane is weak, skin diseases such as blister formation may occur. Accordingly, to observe the formation of basement membrane in dermis 6 weeks after wound healing, laminin staining was carried out, and the results are represented in FIG. 12.

Figure 12:
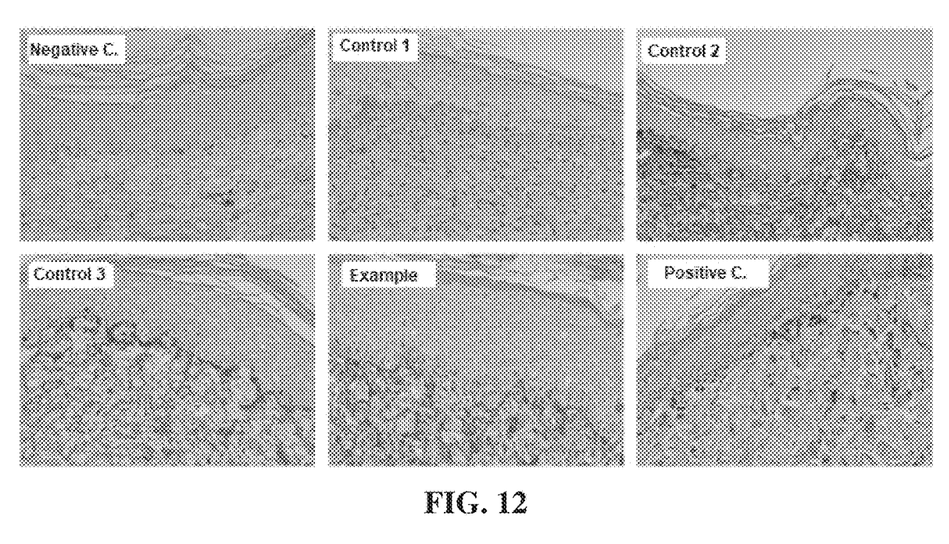
FIG. 12 is optical microscope photographs of the tissues obtained after 6 weeks of wound healing with laminin staining and 200× magnification.

As can be seen from FIG. 12, in the Example group and Control 3 group laminin in brown was observed as similar with the Positive Control group, and in the Control 2 group much laminin was expressed in dermal layer other than the basement membrane. However, in the Negative Control group and Control 1 group laminin was expressed very weakly.

What is claimed is:

1. A wound dressing comprising 5 to 20% by weight of fiberized acellular dermal matrix, 0.5 to 5% by weight of biocompatible polymer and 75 to 94.5% by weight of water,
   wherein the fiberized acellular dermal matrix is prepared by pulverizing acellular dermal matrix with a cutting mill,
   the fiberized acellular dermal matrix is in the form of cotton, and
   the fiberized acellular dermal matrix has a fiber length of 200 to 1,000 μm,
   wherein the biocompatible polymer is gelatin, hyaluronic acid, collagen, poloxamer, or a mixture thereof, and
   wherein the wound dressing is in a dosage form of a paste.

2. The wound dressing according to claim 1, wherein the biocompatible polymer is gelatin.

3. The wound dressing according to claim 1, which has the viscosity of 10,000 to 20,000 cP.

4. The wound dressing according to claim 1, which comprises 8 to 12% by weight of fiberized acellular dermal matrix, 1 to 2% by weight of biocompatible polymer and 86 to 91% by weight of water.

5. A method for preparing a wound dressing which comprises:
   pulverizing acellular dermal matrix by using a cutting mill to obtain fiberized acellular dermal matrix;
   dissolving biocompatible polymer in water to obtain a biocompatible polymer aqueous solution;
   mixing the fiberized acellular dermal matrix and the biocompatible polymer aqueous solution to obtain a mixture comprising 5 to 20% by weight of fiberized acellular dermal matrix, 0.5 to 5% by weight of biocompatible polymer and 75 to 94.5% by weight of water; and
   sterilizing the mixture,
   wherein the fiberized acellular dermal matrix is in the form of cotton and has a fiber length of 200 to 1,000 μm,
   the biocompatible polymer is gelatin, hyaluronic acid, collagen, poloxamer, or a mixture thereof, and
   the wound dressing is in the form of a paste.

6. The method for preparing a wound dressing according to claim 5, wherein the acellular dermal matrix is prepared by a method comprising:
   a) removing epidermis of allograft skin;
   b) removing cells in dermis;
   c) mixing glycerol, propylene glycol and a basic solvent or solution;
   d) dissolving sucrose in the solution to a final concentration of 20 to 40% by weight to obtain a cryoprotectant;
   e) penetrating the cryoprotectant into the skin from which epidermis and cells in dermis are removed; and
   f) freeze-drying the cryoprotectant-penetrated skin.

7. The method for preparing a wound dressing according to claim 6, wherein the mixing ratio of glycerol, propylene glycol and the basic solvent or solution is 0.5~2:0.5~2:6~10, based on weight.

8. The method for preparing a wound dressing according to claim 6, wherein the basic solvent or solution is selected from the group consisting of distilled water, normal saline, phosphate-buffered saline, Hank's balanced salt solution, Tris-buffered saline, N-Tris(hydroxymethyl)methyl-3-aminopropanesulfonic acid buffer, Bicine buffer, 4-(2-hydroxyethyl)-1-piperazineethanesulfonic acid buffer, N-Tris(hydroxymethyl)methyl-2-aminoethanesulfonic acid buffer, piperazine-N,N'- bis(2-ethanesulfonic acid) buffer, cacodylate buffer, 2-(N- morpholino)ethanesulfonic acid buffer, Minimum Essential Media, Dulbecco's Modified Eagle Media, RPMI 1640, Iscove's Modified Dulbecco's Media, Defined Keratinocyte-SFM without bovine pituitary extract, Keratinocyte-SFM with bovine pituitary extract, and a mixture thereof.

9. The method for preparing a wound dressing according to claim 5, wherein the biocompatible polymer is dissolved in water at the temperature of 50 to 70° C.

10. The method for preparing a wound dressing according to claim 5, wherein the sterilization is carried out by radiation sterilization.

* * * * *